(12) United States Patent
Rafter et al.

(10) Patent No.: US 6,503,203 B1
(45) Date of Patent: Jan. 7, 2003

(54) AUTOMATED ULTRASOUND SYSTEM FOR PERFORMING IMAGING STUDIES UTILIZING ULTRASOUND CONTRAST AGENTS

(75) Inventors: Patrick G. Rafter, Windham, NH (US); Heinrich Beckermann, Herrenberg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 39 days.

(21) Appl. No.: 09/681,129

(22) Filed: Jan. 16, 2001

(51) Int. Cl.[7] .................................................. A61B 8/14
(52) U.S. Cl. ...................................................... 600/458
(58) Field of Search ........................ 600/437, 442–458, 600/420, 408, 431; 73/625, 626; 367/7, 11, 130, 138; 324/306

(56) References Cited

U.S. PATENT DOCUMENTS

| | | | | |
|---|---|---|---|---|
| 4,796,634 A | * | 1/1989 | Huntsman et al. | 600/457 |
| 5,325,859 A | * | 7/1994 | Ishihara et al. | 600/443 |
| 5,553,619 A | * | 9/1996 | Prince | 600/420 |
| 5,776,063 A | * | 7/1998 | Dittrich et al. | 600/408 |
| 5,797,396 A | * | 8/1998 | Geiser et al. | 382/128 |
| 5,980,460 A | * | 11/1999 | Ostensen et al. | 600/454 |
| 6,030,344 A | * | 2/2000 | Guracar et al. | 600/447 |
| 6,245,019 B1 | * | 6/2001 | Kamiyama | 600/458 |
| 6,311,085 B1 | * | 10/2001 | Meaney et al. | 324/306 |
| 6,317,623 B1 | * | 11/2001 | Griffiths et al. | 600/431 |

* cited by examiner

*Primary Examiner*—Marvin M. Lateef
*Assistant Examiner*—Ali M. Imam
(74) *Attorney, Agent, or Firm*—John Vodopia

(57) ABSTRACT

An ultrasound system that has transmit and receive circuitry that, pursuant to a plurality of image settings, transmits ultrasound signals into a patient, receives echoes from a patient and outputs a signal representative of the echo. Control circuitry is provided that sequentially adjusts the image settings so as to cause the transmit and receive circuitry to have a sequence of imaging configurations during an ultrasound imaging study. A memory may be provided that stores a plurality of state diagrams, each defining a sequence of imaging configurations for a particular imaging study, which are accessible by the control circuitry, wherein the control circuitry accesses a selected state diagram to conduct an imaging study. Such a system is particularly useful for imaging studies that utilize contrast agents.

27 Claims, 2 Drawing Sheets

AUTOMATED ULTRASOUND SYSTEM FOR PERFORMING IMAGING STUDIES UTILIZING ULTRASOUND CONTRAST AGENTS

BACKGROUND OF INVENTION

The present invention relates to method and apparatus which automate imaging studies that require mode changes, such as studies that utilize contrast agents. The present invention is particularly relevant to: stress, echo studies; perfusion studies; coronary flow reserve studies; and the generation of blood flow/volume curves.

A relatively recent advance in ultrasonic imaging is the use of contrast agents to enhance ultrasound returns. Contrast agents are substances which strongly interact with ultrasound waves and return echoes which may be clearly distinguished from those returned by blood and tissue. Contrast agents generally comprise coated gas microbubbles that are stable in the body for a significant period of time. The coating shells serve to protect the gas from diffusion into the blood stream, but at moderately high ultrasound pressure amplitudes the shells of the microbubbles rupture (creating an easily detectable ultrasonic event) freeing the internal gas and substantially eliminating the detectability thereof by incident ultrasound waves.

Contrast agents provide a non-linear behavior in certain acoustic fields. Such behavior is readily detectable by use of known algorithms. Contrast agents are useful for imaging of the body's vascular system and are injectable through the veins and arteries. They are subsequently filtered from the blood stream by the lungs, kidneys and liver. Contrast agents are currently approved for left ventricular opacification (LVO) and may soon be approved for myocardial perfusion studies.

The present inventors believe that a variety of ultrasound imaging studies could take advantage of contrast agents to obtain various views of the patient. As used herein the term ultrasound imaging study (or more simply imaging study) refers to an examination that requires the creation of a series of ultrasound images (or a series of collection of images such as with cineloops) that each require the ultrasound system, used to obtain the images, to be configured in a different mode. The collection of image settings required to configure the ultrasound system to image in a specific manner is collectively referred to herein as the imaging configuration. Accordingly, each imaging configuration has a variety of associated image settings which control the operation of the ultrasound system monitoring the patient during the imaging study. Some examples of imaging studies that might benefit from the use of contrast agents include stress echo, Left Ventricular Opacification/Myocardial Perfusion studies and generation of blood flow/volume curve studies.

A stress echo study is a safe, noninvasive study that uses ultrasound (sound waves) to evaluate the function and blood flow of the heart in response to exercise. A stress echo study is typically performed by having a patient pedal a stationary bicycle while lying on a bed. Some stress studies are given using a treadmill where the patient's heart function are continuously monitored for eletrocardiographic changes and also wall motion abnormalities. A variety of devices are used to monitor the patient, including an electrocardiograph machine (ECG), an ultrasound imaging system, a blood pressure cuff and a mask. The ECG records your heart's electrical activity from information received through electrodes, taped to a patient's back and chest. The ultrasound imaging system monitors the heart's activity and provides quantitative and qualitative information about the functioning of the heart. The blood pressure cuff constantly monitors the patient's blood pressure, while the mask may be used during the study to measure oxygen use.

Sometimes a drug such as adenosine, dobutamine, or persantine is used, instead of a treadmill, to simulate the heart's reactions to exercise. These drugs are safe and reasonably well tolerated, and are usually only given when the body is unable to perform the stress study, for instance if a patient is particularly out of shape, has lost limbs, or is severely arthritic.

During a stress study, a study giver will gradually increase the speed and incline of the exercise device every two to three minutes while monitoring the patient's heart through the various devices listed above. The stress study usually lasts between six and ten minutes. Throughout the study,.the heart's function and/or oxygen flow in response to increased "challenges" to the heart will be closely observed. Stress studies may enable a doctor to estimate the severity of blockages. Further, if the patient has just undergone balloon angioplasty or bypass surgery, a stress study helps doctors monitor the success of the procedure as well as determine an appropriate rehabilitation program. Unusual changes in ECG patterns or blood pressure, and/or unusual shortness of breath or chest pain, are possible symptoms of coronary artery obstruction.

Ultrasound systems enhance stress study by facilitating the detection of ischemia. However, such detection requires the acquisition of multiple views (at least four) during the study. While each of the views is imaged using the same imaging mode, this is still quite a challenge on a moving patient during a rather short time period. U.S. Pat. No. 5,152,290 teaches a method for acquiring stress echo images to facilitate accurate comparisons of views using .a constant acoustic frame rate. The assignee of the present application, AGILENT TECHNOLOGIES INC., has implemented an automated stress package on the SONOS 5500 system that facilitates the collection of ultrasound images during a stress study: Such systems are highly successful for basic imaging procedures where the imaging configurations utilized do not require a mode change.

Contrast agents have the potential to dramatically improve the qualitative and quantitative information obtained during stress echo studies by improving and speeding up visualization of the endocardium. However, the use of contrast agents requires different imaging configurations, e.g. modes of imaging, requiring complex. parametric changes during imaging. For example, a high mechanical index (MI a measure of the power output by an ultrasonic transducer) is-required for good tissue harmonic imaging (one of the standard imaging modes for stress echo studies), while low MI's are required for LVO contrast imaging. Such a switch requires a battery of parametric changes to the imaging settings making the integration of contrast imaging with stress echo studies unduly complicated. Further, additional modes of contrast imaging are being perfected, including harmonic power Doppler and pulse inversion imaging. Trying to manually integrate such contrast agent imaging modes with the current imaging modes used during stress echo studying is almost impossible because of the complexity of the operator actions required to reconfigure the ultrasound imaging system.

If contrast agent perfusion studies are approved, such studies will face similar problems in that system parameters and imaging modes will have to be modified quickly between: images without contrast agents (employing high MI tissue harmonics); images for LVO (employing low MI, near-field focus, and special detection techniques such as pulse inversion); and images for perfusion (employing high MI and special triggering techniques such as frame rate control, harmonic power Doppler, power modulation, or pulse inversion Doppler). It is anticipated that perfusion studies will require images from at least four viewpoints. It is further anticipated that images using at least three different imaging modes (2D without contrast, LVO with contrast, and perfusion) will be necessary from each view point, making for a total of twelve images with mode and parametric switches in between each image.

Another contrast agent imaging study is current being explored that generates a blood flow/volume curve. The curve is generated by triggering image acquisition based on cardiac triggers and varying the number of beats between cardiac triggers from 1 cardiac cycle to up to 10 cardiac cycles or more. This study requires the use of ultrasound exhibiting a specific set of parameters including frequency, PRF's, MI, transmit cycles, etc... A varieties of factors must be closely controlled during the study:.contrast infusion rate, contrast destruction rate (requiring fine control over the ultrasound signal), triggering, and image optimization. To complicate things, it is likely that each view may require a different contrast agent infusion rate because of view dependent attenuation.

Another type of imaging study that could potentially use contrast agents is a coronary flow reserve study which attempts to identify ischema. Basically, this type of study calls for the location of a coronary artery, which has proven difficult. Once a suitable section of artery has been identified, the artery is monitored at rest and under stress using, among other modes, Doppler. By comparing at rest values with stress values ischema can be quantified. Coronary flow reserve studies have proven difficult to implement without contrast agent. Using contrast agents in conjunction with specialized imaging modes, such as ultra-harmonics, holds the promise of helping the user locate coronary arteries, thereby facilitating coronary flow reserve studies. However, a variety of system settings need adjustment during the study, including Doppler system settings such as scale and gate, making the manual implementation of coronary flow studies improbable due to the difficulty of reproducing the various settings during the course of the study.

In summary, it appears that imaging studies utilizing contrast agents are going to be very complicated and require the rapid changing of imaging modes and parametric information during the study. At the present time, the barriers to acceptance outweigh the clinical benefit of imaging studies incorporating contrast agents. However, this situation is expected to change. Accordingly, the inventors have recognized a need to simplify such studies by automating the rapid changing of imaging modes and parametric information during the study.

SUMMARY OF INVENTION

An ultrasound system having transmit and receive circuitry that, pursuant to a plurality of image settings, transmits ultrasound signals into a patient, receives echoes from a patient and outputs a signal representative of the echo. Control circuitry is provided that sequentially adjusts the image settings so as to cause the transmit and receive circuitry to have a sequence of imaging configurations during an ultrasound imaging study using contrast agents. A memory may be provided that stores a plurality of state diagrams, each defining a sequence of imaging configurations for a particular imaging study, which are accessible by the control circuitry, wherein the control circuitry accesses a selected state diagram to conduct an imaging study.

BRIEF DESCRIPTION OF DRAWINGS

These and other objects and advantages of the invention will become apparent and more readily appreciated from the following description of the preferred embodiments, taken in conjunction with the accompanying drawings of which.

DETAILED DESCRIPTION

Figure 1:
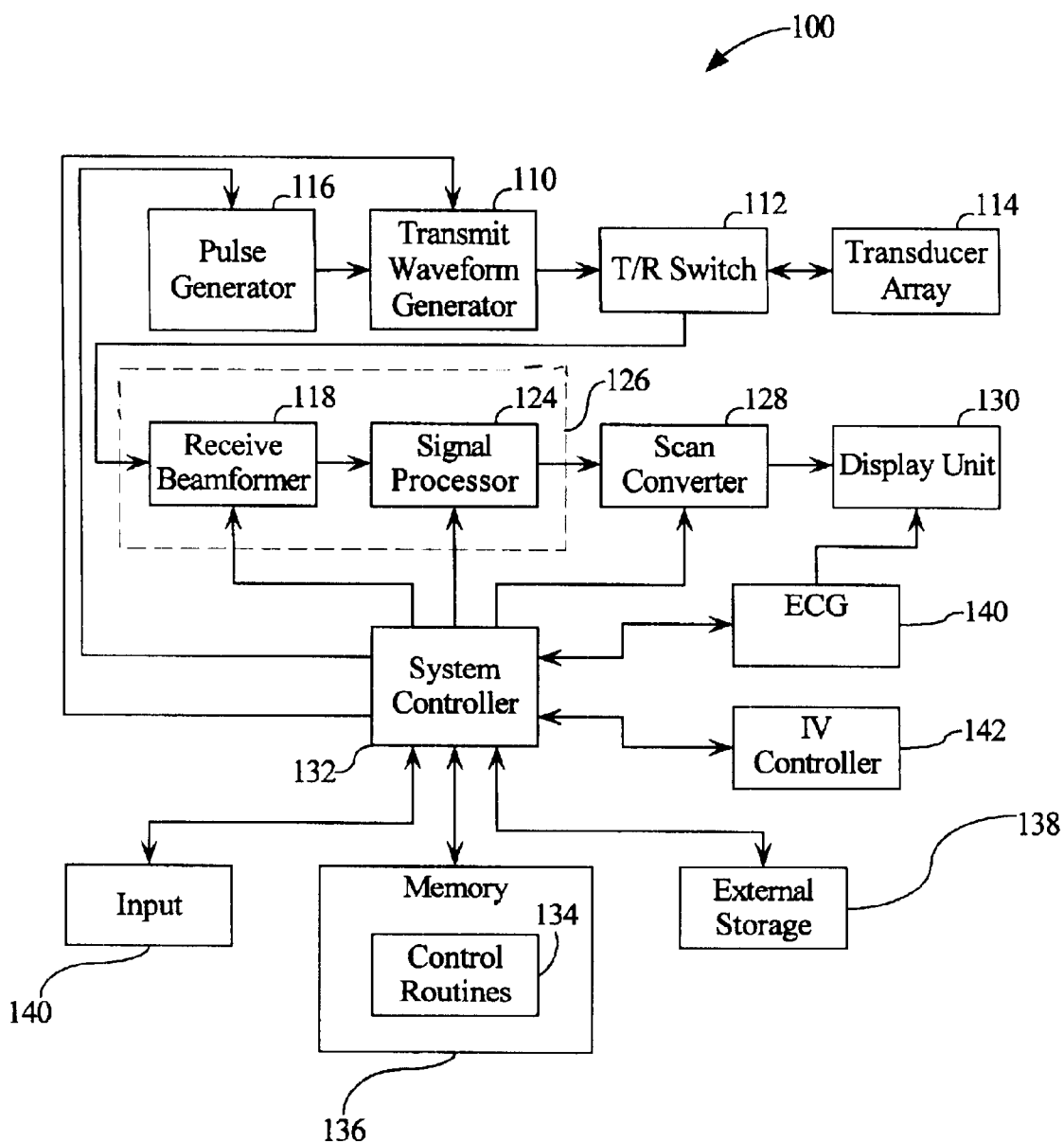
FIG. 1 is a block diagram of an ultrasound system in accordance with the preferred embodiments of the present invention.

Reference will now be made in detail to the present preferred embodiments of the present invention, examples of which are illustrated in the accompanying drawings, wherein like reference numerals refer to like elements throughout.

The present invention provides an automated system for performing imaging studies involving contrast agents. In particular, the present invention provides an ultrasound imaging apparatus that stores internal state diagrams and uses same to attempt to predict a next step of the user and adjust an imaging mode and image settings of the ultrasound imaging apparatus to prepare for the performance of such a next step.

The detailed description which follows is presented in terms of routines and symbolic representations of operations of data bits within a memory, associated processors, and possibly networks, and network devices. These descriptions and representations are the means used by those skilled in the art effectively convey the substance of their work to others skilled in the art. A routine is here, and generally, conceived to be a self-consistent sequence of steps or actions leading to a desired result. Thus, the term "routine" is generally used to refer to a series of operations performed by a processor, be it a central processing unit of an ultrasound system, or a secondary processing unit of such an ultrasound system, and as such, encompasses such terms of art as program, "objects," "functions," "subroutines," and "procedures." In general, the sequence of steps in the routines require physical manipulation of physical quantities. Usually, though not necessarily, these quantities take the form of electrical or magnetic signals capable of being stored, transferred, combined, compared or otherwise manipulated. Those of ordinary skill in the art conveniently refer to these signals as "bits", "values", "elements", "symbols", "characters", "images", "terms", "numbers", or the like. It should be recognized that these and similar terms are to be associated with the appropriate physical quantities and are merely convenient labels applied to these quantities.

In the present case, the routines and operations are machine operations to be performed in conjunction with human operators. Useful machines for performing the operations of the present invention include the AGILENT TECHNOLOGIES SONOS 5500 and other similar devices. In general, the present invention relates to method steps, software, and associated hardware including computer readable medium, configured to store and/or process electrical or other physical signals to generate other desired physical signals.

The apparatus set forth in the present application is preferably specifically constructed for the required purpose, i.e. ultrasound imaging, but the methods recited herein may operate on a general purpose computer or other network devices selectively activated or reconfigured by a routine stored in the computer and interface with the necessary ultrasound imaging equipment. The procedures presented herein are not inherently related to any particular ultrasonic system, computer or other apparatus. In particular, various machines may be used with routines in accordance with the teachings herein, or it may prove more convenient to construct more specialized apparatus to perform the required method steps. In certain circumstances, when it is desirable that a piece of hardware possess certain characteristics, these characteristics are described more fully in the following text. The required structures for a variety of these machines may appear in the description given below. Machines which may perform the functions of the present invention include those manufactured by such companies as AGILENT TECHNOLOGIES and PHILIPS, as well as other manufacturers of ultrasound equipment.

With respect to the software described herein, those of ordinary skill in the art will recognize that there exists a variety of platforms and languages for creating software for performing the procedures outlined herein. Those of ordinary skill in the art also recognize that the choice of the exact platform and language is often dictated by the specifics of the actual system constructed, such that what may work for one type of system may not be efficient on another system.

FIG. 1 is a block diagram of an ultrasound imaging system 100 for use with preferred embodiments of the present invention. It will be appreciated by those of ordinary skill in the relevant arts that the ultrasound imaging system 100, as illustrated in FIG. 1, and the operation thereof as described hereinafter is intended to be generally representative of such systems and that any given system may differ significantly from that shown in FIG. 1, particularly in the details of construction and operation of such system. As such, the ultrasound imaging system 100 is to be regarded as illustrative and exemplary and not limiting as regards the invention described herein or the claims attached hereto.

A transmit beamformer 110 is coupled through a transmit/receive (T/R) switch 112 to a transducer array 114, which includes an array of transducer elements. The T/R switch 112 typically has one switch element for each transducer element. The transmit beamformer 110 receives pulse sequences from a pulse generator 116. The transducer array 114, energized by the transmit beamformer 110, transmits ultrasound energy into a region of interest (ROI) in a patient's body and receives reflected ultrasound energy, or echoes, from various structures and organs within the patient's body. As is known in the art, by appropriately delaying the pulses applied to each transducer element by the transmit beamformer 110, a focused ultrasound beam is transmitted.

The transducer array 114 is also coupled, through the T/R switch 112, to a receive beamformer 118. Ultrasound energy from a given point within the patient's body is received by the transducer elements at different times. The transducer elements convert the received ultrasound energy to transducer signals which may be amplified, individually delayed and then summed by the receive beamformer 118 to provide a beamformer signal that represents the received ultrasound level along a desired receive line. The receive beamformer 118 may be a digital beamformer including an analog-to-digital converter for converting the transducer signals to digital values. As known in the art, the delays applied to the transducer signals may be varied during reception of ultrasound energy to effect dynamic focusing. The process is repeated for multiple scan lines to provide signals for generating an image of the region of interest in the patient's body. The receive beamformer 118 may, for example, be a digital beamformer of the type used in the AGILENT SONOS 5500 ultrasound system manufactured and sold by AGILENT TECHNOLOGIES.

The scan pattern may be a sector scan, wherein scan lines typically originate at the center of the transducer array 114 and are directed at different angles. Linear, curvilinear and other scan patterns may also be utilized. Furthermore, the scan pattern may be two-dimensional or three-dimensional. In an alternative system configuration, different transducer elements are used for transmitting and receiving. In that configuration, the T/R switch 112 is not required, and the transmit beamformer 110 and the receive beamformer 118 are connected directly to the respective transmit and receive transducer elements.

The beamformer signals are applied to a signal processor 124 which processes the beamformer signal for improved image quality and may include processes such as harmonic processing. The receive beamformer 118 and the signal processor 124 constitute an ultrasound receiver 126. The output of the signal processor 124 is supplied to a scan converter 128 which converts sector scan or other scan pattern signals to conventional raster scan display signals. The output of the scan converter 128 is supplied to a display unit 130, which displays an image of the region of interest in the patient's body. In the case of a three-dimensional scan pattern, the scan converter 118 may be replaced by an image data buffer that stores the three-dimensional data set and a processor that converts the three-dimensional data set to a desired two-dimensional image.

A system controller 132 provides overall control of the system. The system controller 132 performs timing and control functions and typically includes a microprocessor operating under the control of control routines 134, stored in a memory 138. As will be discussed in detail below, the control routines 134 include a variety of routines to automate the ultrasound system 100 for imaging studies utilizing ultrasound contrast agents. The system controller 132 also utilizes a memory 136 to store intermediate values, including image settings describing the operation of the ultrasound imaging system 100. Examples of such image settings include MI, mode, number of rise, frequency, gain, focus frame rate, detection technique, etc... The memory 136 also store the state diagrams discussed herein below. External storage 138 may be utilized for more permanent and/or transportable storage of data. Examples of devices suitable for use as the suitable external storage 138 include a floppy disk drive, a CD-ROM drive, a videotape unit, etc.

The ultrasound system 100 shown in FIG. 1 is also provided with an ECG interface 140 that provides ECG data to the system controller 132 and display data to the display unit 130. The ECG data can be use to facilitate triggering in a known manner. Further an IV controller 142 is provided to automate the delivery of contrast agent and/or Dobutamine or other chemical used during the study. Automated control of an IV is known in the art and may be based on time, ECG signals, contrast agent density, etc...

Figure 2:
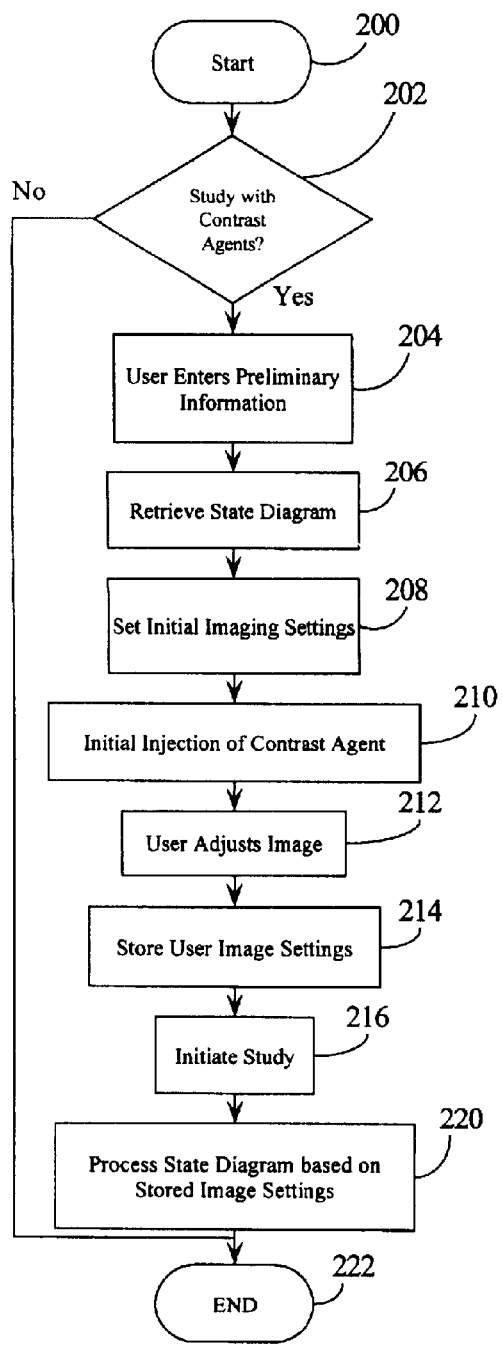
FIG. 2 is a flow chart of a routine for performing an imaging study in accordance with the preferred embodiments of the present invention.

FIG. 2 is a flow chart of a routine for performing an imaging study in accordance with the preferred embodiments of the present invention. The routine starts in step 200 and a determination is made in step 202 as to whether the study involves the use of contrast agents. If no contrast agents are to be used the routine ends in step 222. Otherwise the routine goes to step 204 and receives preliminary information from the user conducting the study.

The preliminary information typically comprises patient data, date, time, type of study, name of contrast agent to be used, method of administering the contrast agent, etc. . . . Next, in step 206, the routine retrieves the appropriate state diagram. for the type of study being conducted. A state diagram can be considered a protocol that lists a sequence of states entered into by the ultrasound system 100 during the imaging study being performed. Each state provides a plurality of image settings that, once entered, cause the ultrasound system 100 to enter a specific imaging configuration. Each state also has a defined subsequent state to enter upon completion of the present state either stored with the state or with a record associate with the overall state diagram. Thus, the state diagram stores data related to a series of imaging configurations, in essence relating a plurality of image settings to each state. During the imaging study, the system controller 132 will step.through a series of image configurations, reconfiguring the ultrasound. system 100 by changing imaging setting such as the mode of imaging, gain, contrast, depth, etc . . . Depending on the nature of the control routines 134, the state diagram can comprise actual code for controlling the ultrasound system 100, or so-called plain English indications understandable by a user such as a technician or medical personnel. The benefit of plain English instruction is that they can be entered and modified by users of the system, with the drawback being that they need to be interpreted prior to execution on the ultrasound system 100.

Tables 1 through 10 represent a simplified portion of a state diagram adopting the plain English model. In this example, each state, e.g. imaging configuration,. that the ultrasound system 100 enters is defined in a separate table (tables 1–5) termed a state table, which is referenced in a view table (tables 6–9) that provides an order of states for a variety of views. An additional table (table 5) provides a set of impulse parameters for use with real-time MCE with impulse view (table 4). In this case, the user is able to press a button to output a signal (the so-called impulse) that disrupts the contrast agents. The settings for the impulse are stored, at least in this example, in a separate table. A sample study table (Table 10) is provided that collects the various views into stages of the study. Table 10 shows a simple stress test that utilizes Dobutumine and has three stages: rest; low dose Dobutumine; and high dose Dobutumine. Thus, in this example, each state diagram is comprised of a study table referencing and at least one view table which in turn references at least one state table. Those of ordinary skill in the art will recognize that any data structure capable of relating data in a relational or hierarchical manner will enable the present invention.

TABLE 1

| State | Endocardial Borders |
|---|---|
| Mode | Tissue Harmonics with Pulse Inversion |
| Transmit Frequency | 1.3 MHz |
| Receive Frequency | 2.6 MHz |
| Receive filter Bandwidth | 1.3 MHz |
| Receive Filter | Gaussian |
| Transmit Waveform | Gaussian |
| Cycles | 2 |
| Frame Rate | 30 Hz |
| MI | 1.6 |
| Focus | 18 cm |
| Number of focal zones | 1 |
| Transmit Apodization | Hamming Window |

TABLE 1-continued

| TGC's | On with a nominal curve |
|---|---|
| LGC's | On with a nominal curve |
| Overall Gain | Medium |
| Post-Processing Curve | C |
| Dynamic Range | 50 dB |
| Infusion rate | Off |

TABLE 2

| State | LVO |
|---|---|
| Mode | Pulse Inversion |
| Transmit Frequency | 1.6 MHz |
| Receive Frequency | 3.2 MHz |
| Receive filter Bandwidth | 0.80 MHz |
| Receive Filter | Gaussian |
| Transmit Waveform | Gaussian |
| Cycles | 4 |
| Frame Rate | 25 Hz |
| MI | 0.3 |
| Transmit Focus | 6 cm |
| Transmit Apodization | Hamming Window |
| TGC's | On with a nominal curve |
| LGC's | On with a nominal curve |
| Overall Receive Gain | High |
| Post-Processing Curve | A |
| Dynamic Range | 30 dB |
| Infusion Rate | 15 cc/hr |

TABLE 3

| State | MCE |
|---|---|
| Mode | Power Modulation |
| Transmit Frequency | 1.3 MHz |
| Receive Frequency | 3.6 MHz |
| Receive filter Bandwidth | 0.80 MHz |
| Receive Filter | Gaussian |
| Transmit Waveform | rectangular |
| Cycles | 8 |
| Frame Rate | Triggered |
| Sequence | 1-3-5-7-9 Cardiac beats |
| ECG Delay | 250 msec (on T-wave) |
| MI | 1.6 |
| Focus | 10 cm |
| Transmit Apodization | Rectangular window |
| TGC's | On with a nominal curve |
| LGC's | On with a nominal curve |
| Overall Receive Gain | Medium |
| Post-Processing Curve | A |
| Dynamic Range | 30 dB |
| Infusion Rate | 25 cc/hr |

TABLE 4

| State | Real-time MCE (with Impulse) |
|---|---|
| Mode | Power Modulation |
| Transmit Frequency | 1.7 MHz |
| Receive Frequency | 1.7 MHz |
| Receive filter Bandwidth | 0.9 MHz |
| Receive Filter | Gaussian |
| Transmit Waveform | Gaussian |
| Cycles | 1 |
| Frame Rate | 20 Hz |
| MI | 0.12 |
| Focus | 14 cm |
| ECG Acquisition Delay | Acquire at 300 msec from R-wave |
| Focus | 10 cm |
| Transmit Apodization | Rectangular window |
| TGC's | On with a nominal curve |
| LGC's | On with a nominal curve |
| Overall Receive Gain | High |
| Post-Processing Curve | A |

TABLE 4-continued

| | |
|---|---|
| Dynamic Range | 25 dB |
| Infusion Rate | 50 cc/hr |

TABLE 5

| | |
|---|---|
| Frames | 5 |
| MI | 1.7 |
| Transmit frequency | 1.0 MHz |
| Transmit Waveform | rectangular window |
| Transmit Apodization | rectangular window (all elements on) |
| Transmit Cycles | 8 |
| Transmit Pulses | 5/line |
| Transmit Focus | 20 cm |
| Frame rate | 60 Hz |

TABLE 6

| View | Apical 4 |
|---|---|
| State 1 | 1 |
| State 2 | 2 |
| State 3 | 3 |
| State 4 | 4 |

TABLE 7

| View | Apical 2 |
|---|---|
| State 1 | 1 |
| State 2 | 2 |
| State 3 | 3 |

TABLE 8

| View | Parasternal Long |
|---|---|
| State 1 | 1* |
| State 2 | 2* |

TABLE 9

| View | Parasternal Short |
|---|---|
| State 1 | 1* |
| State 2 | 2* |

*Most likely will use a slightly modified form of the table listed, but the record has been simplified for explanatory purposes Most likely will use a slightly modified form of the table listed, but the record has been simplified for explanatory purposes

TABLE 10

STRESS STUDY

| Table | Stage |
|---|---|
| 6 | Rest |
| 7 | " |
| 8 | " |
| 9 | " |

TABLE 10-continued

STRESS STUDY

| Table | Stage |
|---|---|
| 6 | Low Dose Dobutumine |
| 7 | " |
| 8 | " |
| 9 | " |
| 6 | High Dose Dobutumine |
| 7 | " |
| 8 | " |
| 9 | " |

Once the correct state diagram has been identified and retrieved, the ultrasound system 100 is configured by loading baseline settings, typically stored as a separate table in the state diagram, in step 208. Next, in step 210, an initial injection of contrast agent is performed. Subsequently, in step 212, the user of the ultrasound system adjusts the imaging settings to his or her preference. In perhaps the simplest form of adjustment, the user sets various global value that are to be used in each imaging mode, such as MI, focus, and frame rate. Once the settings have been adjusted to the users liking, the routine goes to step 214 and stores the settings adjusted by the user in step 212. It is noted that steps 210 through 214 are optional. In a more complicated form of adjustment, the user may progress through each of the tables related to the selected study adjusting the the values therein. For example, with respect to the study table, the user may wish to rearrange the stages, modify the order of views in each stage, or remove or add stages. Similarly, for each of the views, the user may wish to rearrange the states, modify the order of views in each state, or remove or add states. Finally, with respect to each of the states, the user may adjust the image settings to his or her liking.

In any event, in step 216 the user initiates the stress study. Subsequently, in step 218, the routine accesses the retrieved state diagram and reconfigures the ultrasound system 100 based on a state table for the first imaging configuration of the study. During such processing, as the user indicates completion of the imaging to be performed during each state, the routine accesses the next state table and reconfigures the ultrasound system 100 using the various imaging settings referenced in the the state table. Each state table can also store advancement conditions that, once met, indicate that the study can advance to the next state table. Such conditions may include, for example, the user pressing an acknowledgment key, passage of a certain amount of time, the completion of a suitable number of imaging frames, changes in the patients ECG output, or other definable occurrences. Once the study has been completed, the routine ends in step 220.

Several examples of imaging studies utilizing contrast agent are discussed in detail herein below.

Example 1

Stress Echo with Contrast added for Left Ventricular Opacification

1. User determines need for contrast based on prior examination, starts the routine in step 200 and confirms the use of contrast agent in step 202.

2. In step 204 the user inputs preliminary information into the system including:

contrast agent name (e.g., OPTISON, DEFINITY, etc.)

method of administration (e.g., bolus/continuous infusion)

patient information (weight, height, level of difficulty of windows for imaging, etc.)

type of stress study (Dobutamine, Exercise Stress, etc.)

3. Based on this information, the system selects a state diagram (i.e. selects a study table such as shown in Tables 10), in step 206, which best suits the study. The state diagram preferably includes baseline image settings used to initially set up the system for a defined contrast specific detection technique, such as LVO. Also other important parameters may be included such as the mechanical index, the position of the transmit focus, the "f number", transmit apodization, the type of transmit focus, the transmit waveform shape including frequency and duration, line density, etc. Receive parameters may also be provided for the gain, dynamic range, RF filter, image processing, post processing curve, etc. These settings will be different for different imaging planes. In step 208, these settings are loaded into the appropriate registers (perhaps stored in the memory 136) in the ultrasound system 100 so as to provide an initial configuration. Additionally, the state diagram preferably provides a view order for each stage, for example in a view table, to allow for optimal acquisition of the images in a timely manner. The optimal order of views acquired depends on the patient information, the contrast agent given (i.e., how much attenuation will occur), the method of administration as well as sonographer ease of acquisition.

4. Next in step 210 contrast is injected either as a bolus or infusion. The routine preferably controls the pump, using the IV controller 142, determining when to inject the agent, how much agent to inject, how fast to inject, etc. The routine may also control the pump to get an optimal amount of contrast for LVO. This would add consistency to the study as well as make it easier to conduct.

5. Once a steady state of contrast is attained in the first view, the system settings will likely require tweaking by the user in step 212. This is potentially true of each state for each view acquired. If certain view are better without agent, as the parasternal views often are, user can turn off the pump for these views. As the users adjusts system settings related to the states that will be used during the study the routine stores the settings for each particular state in step 214. An alternative method, for views such as the parasternal view, would be to activate a "no contrast" selection on the system. The system would store this preference and would then alter settings to produce an optimal image for endocardial borders without contrast (i.e., Harmonic imaging, high MI, etc.). A preferred method to assist the user with setting the user image settings is to provide a hierarchical menu relating stages to view and views to states that are to be used during the study (as stored with the selected state diagram) and allow the user to progress through the levels by selecting the desired level from the menu. The user can adjust the values at each level to adjust the order and number of stages, the order and number of views in each stage and the order, number and parameters of each stage in each view.

6. As noted, the system stores all the user image settings for each state in each view to be acquired including infusion/injection pump settings in step 214. These settings are stored internally and used for later stages in the study. If implemented, the desired view order modifications are also remembered and altered for the next part of the examination, where time is much more critical.

7. In step 216 the user initiates the stress study and the stress study is begun, in step 218, with a Dobutamine infusion, exercise, etc. With Dobutamine, as indicated in Table 10, there are several stages of "stress", with each stagle requiring more Dobutamine. With stress tests, time is critical because the images are obtained immediately following the exercise or drug infusion portion while the patient heart is recovering. All views must be acquired within 1 minute or so. Following the state diagram, as modified by the settings stored in step 214, the routine automatically changes imaging parameters/view acquisition. The patient heart rate may be monitored by the ECG interface 140 and the infusion rate/injection amount are changed, with the IV controller 142, if necessary. Oftenhigher heart rates require less agent. During the study, the routine activates each view based on stored settings (either default or as modified in step 212) in an order set forth in the state diagram (potentially as modified in step 212).

Example 2

Contrast Study for Left Ventricular Opacification/Myocardial Perfusion

1. User determines need for contrast based on prior examination and also performs baseline imaging to determine appropriate windows for MCE and appropriate windows for LVO. The user then starts the routine in step 200 and confirms the use of contrast agent in step 202.

2. User inputs information before beginning the study including the following:

Type of MCE study (e.g., Dobutamine, exercise, Dipyridamole, Adenosine infusion, Adenosine bolus, etc.)

Agent to be used (e.g., Optison, Definity, Levovist, etc.)

Method of Administration (e.g., infusion or bolus)

Patient information (weight, height, gender, body type, level of difficulty in each imaging plane, etc.)

imaging views will MCE be done on, which imaging planes will LVO be done on.

Desired Output for quantification (e.g., myocardial blood volume, flow-volume curve, coronary flow reserve, etc.).

3. Based on this information, the system selects a state diagram, in step 206, which best suits the study. The state diagram preferably includes image settings for setting up the system for contrast LVO specific detection techniques and MCE specific detection techniques. The settings might include values for the mechanical index, the position of the transmit focus, the "f number", transmit apodization, the type of transmit focusing, the transmit waveform shape (including frequency and duration), transmit line density, transmit sequence, etc. are selected. Receive. parameters are also selected such as the gain, dynamic range, RF filter, image processing, post processing curve, etc. Triggering information is set based on the user inputs. This includes optimum destruction parameters (number of frames, etc.), whether to trigger (e.g., real-time MCE or triggering), where to trigger e.g., mid-T wave), and triggering sequence used to acquire (e.g., 1-3-5-7-9 cardiac cycles to create the flow volume curve). Triggering may also be view dependent (e.g., real-time Power modulation in the Apical 4 and Harmonic power Doppler for the Apical-2). Additionally, the state diagram preferably provides a view order (including MCE and LVO) to allow for optimal acquisition of the images in a timely manner. The optimal order of views acquired, and the states therein, depends on the patient information, the contrast agent given (i.e., how much attenuation will occur), the method of administration as well as sonographer ease of acquisition.

4. Next in step 210 contrast is injected either as a bolus or infusion. The routine preferably controls the pump, using the IV controller 142, determining when to inject the agent, how much agent to inject, how fast to inject, etc. The routine may also control the pump to get an optimal amount of contrast for LVO/MCE. This would add consistency to the study as well as make it easier.

5. Once a steady state of contrast is attained in the first view, the system settings will likely require tweaking by the user in step 212. This is potentially true of each view acquired. If certain view are better without agent, as the parasternal views in LVO often are, user can turn off the pump for these views. As the users adjusts system settings related to the states and views that will be used during the study the routine stores the settings for each particular view in step 214. An alternative method, for views such as the parasternal view, would be to activate a "no contrast" selection on the system. The system would store this preference and would then alter settings to produce an optimal image for endocardial borders without contrast (i.e., Harmonic imaging, high MI, etc.). A preferred method to assist the user with setting the user image settings is to provide a hierarchical menu relating stages to view and views to states that are to be used during the study (as stored with the selected state diagram) and allow the user to progress through the levels by selecting the desired level from the menu. The user can adjust the values at each level to adjust the order and number of stages, the order and number of views in each stage and the order, number and parameters of each stage in each view.

6. As noted, the system stores all the user image settings for each view acquired including infusion/injection pump settings in step 214 These settings are stored internally and used for later stages in the study. If implemented, the desired view order modifications are also remembered and altered for the next part of the study, where time is much more critical.

7. Next in step 214, the Stress study is begun, with a dipyridamole infusion, adenosine infusion, Dobutamine infusion, exercise, etc. With all of these studies time is of critical importance due to the potential side effects of the pharmacological agents, leaving little time for system control manipulation. With Dobutamine there are several stages of "stress", with each stage requiring more Dobutamine. With Exercise Stress, images are obtained immediately following the exercise portion and the patient heart is recovering. All views must be acquired within 1 minute or so. During the study, the routine activates each view based on stored settings (either default or as modified in step 212) in an order set forth in the state diagram (potentially as modified in step 212). Additionally, patient heart rate or contrast agent intensity in LV is monitored by the system and the infusion rate/injection amount, triggering parameters are changed, via the IV controller 142, if necessary. Often higher heart rates requires less agent, a different triggering point and a different triggering sequence.

In accordance with the foregoing, the present inventors have described an automated ultrasound system for performing imaging studies utilizing ultrasound contrast agents. This represents a significant advance over the prior art which requires significant user involvement to manually reconfigure the ultrasound system for each of a plurality of imaging modes used during the imaging studies. While a few examples of imaging studies were given, those of ordinary skill in the art will recognize the applicability of the present invention to other imaging studies utilizing contrast agents such as coronary flow reserve. studies.

Although a few preferred embodiments of the present invention have been shown and described; it would be appreciated by those skilled in the art that changes may be made in these embodiments without departing from the principles and spirit of the invention, the scope of which is defined in the claims and their equivalents.

We claim:

1. An ultrasound system comprising:
    transmit and receive circuitry that, pursuant to a plurality of image settings, transmits ultrasound signals into a patient, receives echoes from a patient and outputs a signal representative of the echo; and
    control circuitry that sequentially adjusts the image settings based on a sequence of stored image settings so as to cause the transmit and receive circuitry to have a sequence of imaging configurations during an ultrasound imaging study using contrast agents.

2. An ultrasound system, as set forth in claim 1, further comprising:
    an ECG unit that provide ECG data to the control circuitry, wherein the control circuitry triggers the obtaining of images based on ECG data.

3. An ultrasound system, as set forth in claim 1, further comprising:
    an IV controller that, under the control of the control circuitry delivers contrast agent to the patient.

4. An ultrasound system, as set forth in claim 3, wherein the control circuitry controls the IV controller based on the ECG data or the intensity of contrast agent.

5. An ultrasound system, as set forth in claim 1, further comprising:
    a memory that stores a plurality of state diagrams, each defining a sequence of imaging configurations for a particular imaging study,
    accessible by the control circuitry, wherein the control circuitry access a selected state diagram to conduct an imaging study.

6. An ultrasound system, as set forth in claim 5, wherein the control circuitry, responsive to a selected state diagram, sequentially re-configures the transmit and receive circuitry to obtain a sequence of images in accordance with a stress study state diagram.

7. An ultrasound system, as set forth in claim 5, wherein the control circuitry, responsive to a selected state diagram, sequentially re-configures the transmit and receive circuitry to obtain a sequence of images in accordance with a perfusion study state diagram.

8. An ultrasound system, as set forth in claim 5, wherein the control circuitry, responsive to a selected state diagram, sequentially re-configures the transmit and receive circuitry to obtain a sequence of images in accordance with a blood flow/volume curve state diagram.

9. An ultrasound system, as set forth in claim 5, wherein the control circuitry, responsive to a selected state diagram, sequentially re-configures the transmit and receive circuitry to obtain a sequence of images in accordance with a coronary flow reserve study state diagram.

10. An ultrasound system, as set forth in claim 5, wherein the control circuitry enables a user to adjust certain image settings prior to conducting the ultrasound imaging study and modifies the values provided in the selected state diagram based on the image settings adjusted by the user.

11. An ultrasound system, as set forth in claim 5, wherein the control circuitry enables a user to adjust an order of the sequence of configurations.

12. An ultrasound system, as set forth in claim 1, wherein at least one, but not all, of the imaging configurations are adapted for imaging without contrast agent.

13. An ultrasound system, as set forth in claim 1, wherein at least one of the imaging configurations requires a mode change.

14. A method for conducting an ultrasound imaging study with contrast agent, the method comprising:

allowing the user to select a type of study;

creating state diagrams describing the various image settings for each of a plurality of imaging configurations that the ultrasound system will enter into during different types of studies;

based on the selection of the type of study, retrieving one of the state diagrams that most closely resembles the selected type of study; and based on the retrieved state diagram, conducting the selected type of study in conjunction with the use of a contrast agent.

15. A method, as set forth in claim 14, further comprising:

prior to conducting the study, injecting a first bolus of the contrast agent;

subsequent to injecting the first bolus of the contrast agent and prior to conducting the study, allowing the user to adjust image settings of an ultrasound system to produce a satisfactory image; and adjusting image settings in the retrieved state diagram based on the image settings adjusted by the user.

16. A method, as set forth in claim 14, further comprising:

prior to conducting the study, allowing the user to adjust the order of the imaging configurations used during the imaging study.

17. A method, as set forth in claim 14, further comprising:

automatically controlling the injection of contrast agent during the study.

18. A method, as set forth in claim 14, further comprising:

monitoring the patient with an ECG unit; and controlling the injection of contrast agent based o the output of the ECG unit.

19. A method, as set forth in claim 14, wherein the user further selects a desired output.

20. An ultrasound system comprising:

transmit and receive circuitry that, pursuant to a plurality of image settings, transmits ultrasound signals into a patient, receives echoes from a patient and outputs a signal representative of the echo; and control means for sequentially adjusting the image settings based on a sequence of stored image settings so as to cause the transmit and receive circuitry to have a sequence of imaging configurations during an ultrasound imaging study using contrast agents.

21. An ultrasound system comprising:

transmit and receive circuitry that, pursuant to a plurality of image settings, transmits ultrasound signals into a patient, receives echoes from a patient and outputs a signal representative of the echo; and a controller responsive to a hierarchical data structure that sequentially adjusts the image settings based on a sequence of stored image settings so as to cause the transmit and receive circuitry to have a sequence of imaging configurations during an ultrasound imaging study using contrast agents.

22. The ultrasound system, as set forth in claim 21, wherein the hierarchical data structure is organized by a study having at least two stages, each stage having at least one view, wherein each view has at least one state with an associated imaging configuration.

23. The ultrasound system, as set forth in claim 22, wherein the controller permits a user to adjust the order of stages, the order of views within each stage and at least some of the image settings for the states associated with each view.

24. A data structure for an ultrasound system for controlling the ultrasound system during a study utilizing contrast agents, the data structure describing a plurality of stages for the study, each stage having associated views and each view having associated states describing image settings for the ultrasound system that configure the ultrasound system for a specific portion of the study.

25. An ultrasound system comprising:

transmit and receive circuitry that, pursuant to a plurality of image settings, transmits ultrasound signals into a patient, receives echoes from a patient and outputs a signal representative of the echo;

control circuitry that sequentially adjusts the image settings so as to cause said transmit and receive circuitry to have a sequence of imaging configurations during an ultrasound imaging study using contrast agents; and a memory that stores a plurality of state diagrams, each of said state diagrams defining a sequence of imaging configurations for a particular imaging study, accessible by said control circuitry, wherein said control circuitry accesses a selected state diagram to conduct the imaging study;

said control circuitry being arranged to enable a user to adjust certain image settings prior to conducting the imaging study and to modify the values provided in the selected state diagram based on the image settings adjusted by the user.

26. A method for conducting an ultrasound imaging study with contrast agent, the method comprising:

allowing the user to select a type of study;

based on the selection of the type of study, retrieving a state diagram that most closely resembles the selected type of study, the state diagram describing the various image settings for each of a plurality of imaging configurations that the ultrasound system will enter into during the imaging study;

based on the retrieved state diagram, conducting the selected type of study in conjunction with the use of a contrast agent;

prior to conducting the study, injecting a first bolus of the contrast agent;

subsequent to injecting the first bolus of the contrast agent and prior to conducting the study, allowing the user to adjust image settings of an ultrasound system to produce a satisfactory image; and adjusting image settings in the retrieved state diagram based on the image settings adjusted by the user.

27. An ultrasound system comprising:

transmit and receive circuitry that, pursuant to a plurality of image settings, transmits ultrasound signals into a patient, receives echoes from a patient and outputs a signal representative of the echo; and a controller responsive to a hierarchical data structure that sequentially adjusts the image settings so as to cause said transmit and receive circuitry to have a sequence of imaging configurations during an ultrasound imaging study using contrast agents;

said hierarchical data structure being organized by a study having at least two stages, each stage having at least one view, each view having at least one state with an associated imaging configuration;

said controller being arranged to permit a user to adjust the order of stages, the order of views within each stage and at least some of the image settings for the states associated with each view.

* * * * *